United States Patent
Wright et al.

(10) Patent No.: US 9,457,160 B2
(45) Date of Patent: Oct. 4, 2016

(54) CONTAINER FOR THE GENERATION OF THERAPEUTIC MICROFOAM

(71) Applicant: BTG International Limited, London (GB)

(72) Inventors: David Dakin Iorwerth Wright, Buckinghamshire (GB); Anthony David Harman, Henley-on-Thames (GB)

(73) Assignee: BTG INTERNATIONAL LIMITED, London (GB)

( * ) Notice: Subject to any disclaimer, the term of this patent is extended or adjusted under 35 U.S.C. 154(b) by 0 days.

(21) Appl. No.: 14/264,446

(22) Filed: Apr. 29, 2014

(65) Prior Publication Data

US 2014/0343484 A1    Nov. 20, 2014

Related U.S. Application Data

(63) Continuation of application No. 13/862,083, filed on Apr. 12, 2013, now abandoned, which is a continuation of application No. 10/513,911, filed as application No. PCT/GB03/02226 on May 23, 2003, now abandoned.

(30) Foreign Application Priority Data

May 24, 2002    (GB) .................................. 0212047.5

(51) Int. Cl.
*A61M 11/00*    (2006.01)
*A61K 9/12*    (2006.01)
(Continued)

(52) U.S. Cl.
CPC .................. *A61M 11/00* (2013.01); *A61K 9/12* (2013.01); *A61K 9/122* (2013.01); *A61M 11/02* (2013.01);
(Continued)

(58) Field of Classification Search
CPC . A61M 11/00; A61M 11/02; A61M 2202/03
USPC ......... 222/94, 105, 386.5, 389, 399, 402.16; 141/3, 20; 128/200.23
See application file for complete search history.

(56) References Cited

U.S. PATENT DOCUMENTS 3,109,463 A    11/1963    Clemens
3,756,476 A    9/1973    Bonduris
(Continued)

FOREIGN PATENT DOCUMENTS

AU          757 260       9/1999
DE     196 32 329 A2     2/1998
(Continued)

OTHER PUBLICATIONS

Kazuo, K.; "Spray Can Set for Double-Liquid Type Coating Material;"; Patent Abstracts of Japan; JP 2001206466; (Nisshin Industry KK), Jul. 31, 2001 (Abstract).

*Primary Examiner* — J. Casimer Jacyna
(74) *Attorney, Agent, or Firm* — Nixon & Vanderhye P.C.

(57) ABSTRACT

Device containing sclerosant liquid for use in the treatment of blood vessels having an aerosol valve housing containing gas-entry ports. The aerosol valve housing is mounted on a canister having an expandable inner container in which the sclerosant fluid is contained. The expandable inner container is affixed to the outer opening of the canister or to the aerosol valve housing above the valve gas-entry ports so that gas taken from the interior of the expandable inner container can mix with the sclerosant liquid to create a micro foam, such that introduction of pressurized gas through the aerosol valve causes the expandable inner container to inflate to accommodate the pressurized gas.

16 Claims, 6 Drawing Sheets

(51) Int. Cl.
  *B65D 83/42* (2006.01)
  *B65D 83/62* (2006.01)
  *A61M 11/02* (2006.01)

(52) U.S. Cl.
  CPC .......... *B65D 83/425* (2013.01); *B65D 83/62* (2013.01); *A61M 2202/03* (2013.01); *A61M 2205/3344* (2013.01)

(56) References Cited

U.S. PATENT DOCUMENTS

| | | | |
|---|---|---|---|
| 3,788,521 A | 1/1974 | Laauwe | |
| 3,894,659 A * | 7/1975 | Focht | B65D 83/682 222/136 |
| 3,896,970 A | 7/1975 | Laauwe | |
| 3,929,132 A | 12/1975 | Higuchi | |
| 4,067,499 A | 1/1978 | Cohen | |
| 5,126,086 A | 6/1992 | Stoffel | |
| 5,135,137 A | 8/1992 | Rudick | 222/1 |
| 5,343,901 A | 9/1994 | Meshberg | |
| 5,655,194 A | 8/1997 | Landa et al. | 399/238 |
| 5,902,225 A | 5/1999 | Monson | |
| 5,915,595 A | 6/1999 | Dow et al. | |
| 5,979,707 A | 11/1999 | Boden et al. | 222/95 |
| 6,007,529 A | 12/1999 | Gustafsson et al. | |
| 6,098,846 A | 8/2000 | Yazawa et al. | |
| 6,196,275 B1 | 3/2001 | Yazawa et al. | |
| 6,299,024 B1 | 10/2001 | Corba | |
| 6,325,248 B1 | 12/2001 | Corba | |
| 6,332,563 B2 | 12/2001 | Baudin | |
| 6,343,713 B1 | 2/2002 | Abplanalp | |
| 6,354,469 B1 | 3/2002 | Pozzi | 222/189.09 |
| 6,398,771 B1 | 6/2002 | Gustafsson et al. | |
| 6,431,413 B2 | 8/2002 | Corba | |
| 6,432,986 B2 | 8/2002 | Levin | 514/330 |
| 6,464,108 B2 | 10/2002 | Corba | |
| 6,520,377 B2 | 2/2003 | Yquel | |
| 6,588,628 B2 | 7/2003 | Abplanalp et al. | 222/105 |
| 6,920,904 B2 | 7/2005 | Yquel | |
| 7,017,761 B1 | 3/2006 | Kneer | |
| 2001/0027981 A1 | 10/2001 | Yquel | |
| 2002/0003147 A1 | 1/2002 | Corba | |
| 2002/0185501 A1 | 12/2002 | Yquel | |
| 2002/0195167 A1 | 12/2002 | Garcia | |
| 2003/0066847 A1 | 4/2003 | Towfighi | |

FOREIGN PATENT DOCUMENTS

| | | |
|---|---|---|
| DE | 196 32 329 A1 | 12/1998 |
| DE | 100 54 819 A1 | 5/2002 |
| DE | 100 54 819 A1 | 8/2002 |
| EP | 0 494 004 A | 7/1992 |
| EP | 0 656 869 B1 | 6/1995 |
| EP | 0 718 213 A | 6/1996 |
| EP | 0 869 908 B1 | 10/1998 |
| EP | 0 930 147 A2 | 7/1999 |
| EP | 0 972 723 A2 | 1/2000 |
| EP | 0 972 723 B1 | 1/2000 |
| EP | 0 980 835 A2 | 2/2000 |
| EP | 1 027 267 B1 | 8/2000 |
| EP | 1 058 657 B1 | 12/2000 |
| EP | 1 122 190 A1 | 8/2001 |
| EP | 1 132 318 A1 | 9/2001 |
| EP | 1 227 987 B1 | 8/2002 |
| EP | 1 256 526 A1 | 11/2002 |
| FR | 1 547 768 A | 10/1968 |
| GB | 1 602 293 | 11/1981 |
| GB | 2 197 690 A | 5/1988 |
| JP | 5 132010 | 5/1993 |
| JP | 5-132010 A | 5/1993 |
| WO | WO 93/24392 | 12/1993 |
| WO | WO 95/01300 | 1/1995 |
| WO | WO 96/02439 | 1/1996 |
| WO | WO 96 11162 A | 4/1996 |
| WO | WO 96/21605 | 7/1996 |
| WO | WO 97/37628 | 10/1997 |
| WO | WO 98/07639 | 2/1998 |
| WO | WO 98/32675 | 7/1998 |
| WO | WO 00 72821 A | 12/2000 |
| WO | WO 00/72821 A1 | 12/2000 |
| WO | WO 01/08990 A1 | 2/2001 |
| WO | WO 02/02435 A1 | 1/2002 |
| WO | WO 02/36456 A1 | 3/2002 |
| WO | WO 02 41872 A | 5/2002 |

\* cited by examiner

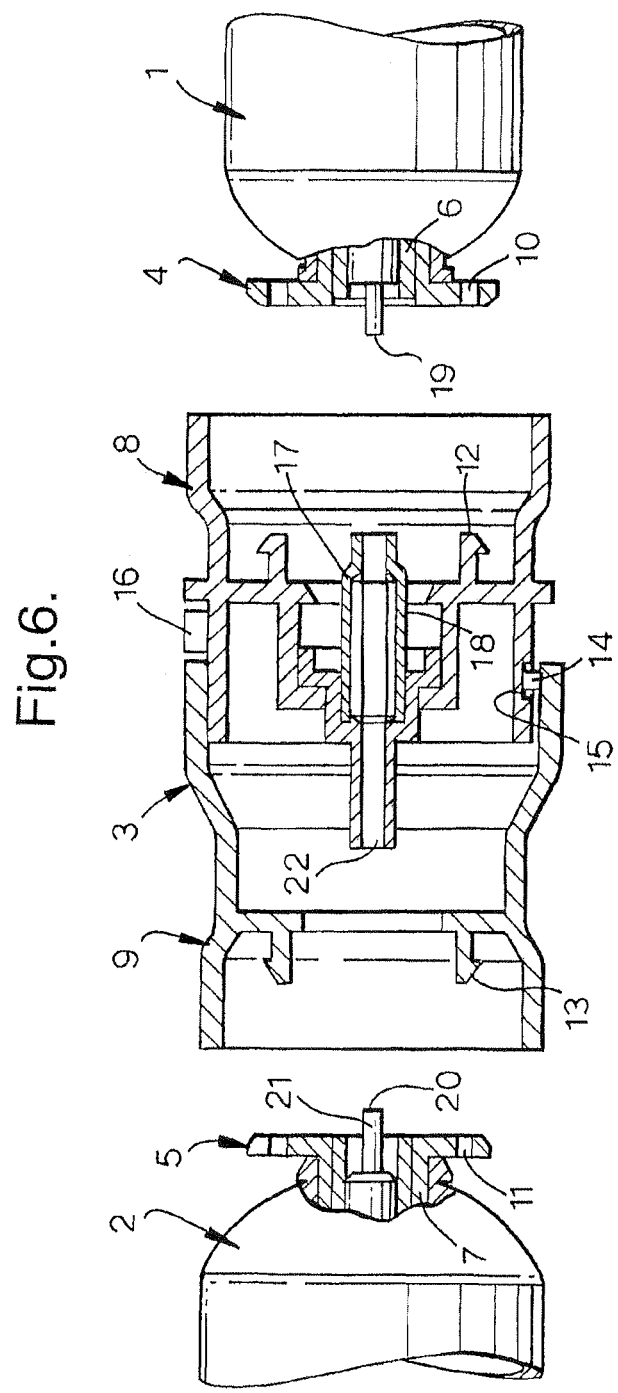

CONTAINER FOR THE GENERATION OF THERAPEUTIC MICROFOAM

This application is a continuation of application Ser. No. 13/862,083 filed Apr. 12, 2013, abandoned, which is a continuation of application Ser. No. 10/513,911, filed Dec. 23, 2004, abandoned, which is a 371 of PCT/GB03/02226, filed May 23, 2003, which claims priority to British Patent Application No. 0212047.5 filed May 24, 2002, the entire contents of each of which are hereby incorporated by reference.

The present invention relates to a method and apparatus for the generation of foam comprising a sclerosing material, particularly a sclerosing liquid, which is suitable for use in the treatment of various medical conditions involving blood vessels, particularly varicose veins and other disorders involving venous malformation.

BACKGROUND OF THE INVENTION

Sclerosis of varicose veins is based on the injection into the veins of liquid sclerosant substances which, by inter alia causing a localised inflammatory reaction, favour the elimination of these abnormal veins. Until recently, sclerotherapy was a technique selected in cases of small and medium calibre varicose veins, those with diameters equal to or greater than 7 mm being treated by surgery. Sclerotherapy and surgery complemented one another but treatment by sclerotherapy continued to be inapplicable to large varicose veins. In these large varicose veins, if a sclerosing liquid was injected, the amount of liquid sclerosant required to fill the entire length of the varicose vein exceeded safe dosage limits at normal sclerosant concentrations, and may be ineffective at the concentrations required to limit the dosage to safe levels. In addition, its concentration in the vein, its homogeneous distribution in the blood, and the time for which it is in contact with the internal walls of the vessel treated were not known.

An injectable microfoam suitable for therapeutic use, on larger veins in particular, has now been developed and is described in EP-A-0656203 and U.S. Pat. No. 5,676,962 (incorporated herein by reference). These patents describe a low-density microfoam produced with a sclerosing substance which, when injected into a vein, displaces blood and ensures that the sclerosing agent contacts the endothelium of the vessel in a known concentration and for a controllable time, achieving sclerosis of the entire segment occupied.

The preparation of such a foam may be carried out with a solution of any sclerosing substance, particularly polidocanol. The method of preparation is to use a small brush attached to a high-speed motor to whip a dilute aqueous solution of the preferred sclerosant to a firm mousse-like consistency in a period of 1-2 minutes under a gas atmosphere containing physiologically acceptable gas mixes. However, this known method requires extemporaneous production of microfoam by the physician, pharmacist or an assistant immediately prior to administration to the patient. Such procedure allows for variation of microfoam sclerosing agent depending upon the person preparing it; microfoam density, gas makeup, bubble size and foam stability all needing attention with respect to the condition being treated.

A solution to this problem is offered in WO 00/72821-A1 (BTG International Limited), incorporated herein by reference, which provides a method and a number of different devices that are capable of producing a uniform injectable microfoam. This microfoam is made with a relatively low concentration of a foamable sclerosing agent and a significant amount of a blood dispersible gas in sterile fashion without volatile liquid propellants or the need for the operator to directly be concerned in the control of its parameters. This application also addresses the perception that large volumes of nitrogen should not unnecessarily be introduced into patients. This is particularly an issue where large vessels are being filled with foam, if air is used as the gas for producing the foam. A preferred form of gas described in WO 00/72821-A1 comprises 50% vol/vol or more oxygen, the remainder being carbon dioxide, or carbon dioxide, nitrogen and trace gases in the proportion found in atmospheric air. Preferably the sclerosing agent is a solution of polidocanol or sodium tetradecyl sulfate in an aqueous carrier, e.g. water, particularly in a saline.

However, the present inventors have identified a potential problem with this formulation, in making the observation that polidocanol, when stored for several months in the presence of oxygen, may slowly decompose. Thus it appears to be undesirable to store polidocanol in a pressurised can in the presence of oxygen, for example as taught in WO 00/72821-A1, as it may result in a reduced shelf life.

One of the specific embodiments described in WO 00/72821-A1 teaches the use of a "bag-on-valve" type aerosol device for the production of a therapeutic microfoam. In this particular device the sclerosant is stored in a bag within an aerosol canister containing physiologically acceptable gas. The device includes an internal valve arrangement. The valve, which is positioned inside the gas filled canister but outside the bag, facilitates mixing of the gas with the sclerosant contained in the bag in order to produce a microfoam. This bag-on-valve construction is intended to impart a degree of orientation-dependence to the device, when compared with a similar device in which the polidocanol solution is free liquid in the bottom of the canister. The potential problem with long-term storage is not addressed.

Co-pending application WO 02/41872-A1 (BTG International Limited) presents a different method and apparatus for the production of a foam suitable for scleropathy. The sclerosant liquid and the oxygen-rich physiologically acceptable blood dispersible gas are stored in separate containers until immediately prior to use, when the blood-dispersible gas is introduced into the container holding the sclerosant liquid until pressure equilibrium is reached between the two connected containers. The mixture of blood-dispersible gas and sclerosant liquid is then released, the components of the mixture interacting upon release of the mixture to form a sclerosing foam. The sclerosant container used is generally a conventional aerosol canister, which has been modified to make it suitable for use in storing and dispensing a sterile sclerosing agent. This apparatus and method produce an excellent sclerosing microfoam, and the use of separate containers for the gas and the sclerosant advantageously avoids the problem of storing the sclerosing fluid, for example, aqueous polidocanol, in the presence of oxygen.

The present inventors have also discovered a number of potential problems with the commercial manufacture of the prior art systems. These relate largely to the difficulties in sterilising and storing aqueous sclerosant solutions, and to the costs of the alternative of aseptic-filled manufacturing techniques. For example, terminal heat sterilisation by autoclaving is the preferred method of ensuring that the aqueous sclerosant is sterile during storage and prior to administration to the patient. WO 00/72821-A1 discloses the use of robust, epoxy coated aluminium aerosol canisters, which have been found to be resistant to the action of polidocanol and oxygen during storage, and to sterilisation by gamma irradiation.

The present inventors have discovered that the heat sterilisation of aqueous polidocanol solution is acceptable in a glass vessel with an inert atmosphere in the container, but may be troublesome in standard aerosol canisters. There is, therefore, a need for a different method and device suitable for the storage of aqueous sclerosant solutions and for the production of a foam suitable for scleropathy.

However, the container that stores the liquid sclerosant is rigid-walled in the prior art, and therefore of fixed internal volume. There are conflicting requirements for this container, as during storage the internal volume of the container holding the sclerosant liquid is best minimised to reduce the amount of inert or compatible gas that is needed during storage (for example nitrogen or carbon dioxide) which would be included in the final, oxygen-rich gas mix after charging, whereas in the final pressurised container, the propellant for the ejection of foam is a compressed gas mix, and a significant container internal volume is required to keep pressure decay at a minimum to preserve foam density and foam ejection rate between specified limits during the ejection of foam from the container. The have also discovered that rigid-walled containers used in the prior art, because they are of fixed internal volume do not meet the conflicting requirements of fixed internal volume.

SUMMARY OF THE INVENTION

It has now surprisingly been found that a conventional "bag-in-can" device can be adapted for use as a device to store sclerosant fluid and used to produce a sclerosing foam. An adapted bag-on-valve device may also be used to similar benefit. Bag-in-can devices are normally used for dispensing gels, such as shaving gels and the like, specifically materials that do not require pre-mixing with a gaseous component prior to use. The conventional bag-in-can device, such as disclosed in GB 1602293 (Metal Box Limited), comprises a canister and a gas-impermeable inner container, usually in the form of a blow-moulded flexible plastic bag, which contains the material to be dispensed. The inner container is fixed to the outer opening of the canister, by means of attachment to the bead of the canister. Thus it differs from a bag-on-valve device, where the inner container is fixed to the aerosol discharge valve. The canister may contain an inert pressurised gas such as carbon dioxide, nitrogen or a noble gas, which the surrounds the bag.

The inventors have identified that these types of devices provide a versatile, relatively inexpensive container for the storage of an aqueous sclerosing agent, such as polidocanol, and, advantageously, can be modified to provide a device suitable for the production of a microfoam suitable for scleropathy. They also have the advantage of minimising the gas volume present during storage, whilst allowing a large volume of pressurised physiologically acceptable gas to be introduced into the container without significant dilution by the storage gas.

Accordingly the first aspect of the invention provides a device containing sclerosant liquid for use in the treatment of blood vessels comprising an aerosol valve housing mounted on a canister having an expandable inner container in which the sclerosant fluid is contained, wherein the expandable inner container is affixed to the outer opening of the canister or to the aerosol valve housing, whereby the introduction of pressurised gas through the aerosol valve causes the expandable inner container to inflate to accommodate the pressurised gas. Preferably the device of the first aspect is configured such that the sclerosant liquid contained therein may be mixed with a pressurised gas comprising a physiologically acceptable blood dispersible gas to produce a sclerosing foam. The expandable inner container may optionally contain a small bag-on-valve inner pouch in which the sclerosant liquid is stored, to afford a degree of orientation independence to the device. Preferably the pressurised gas is stored in a separate container prior to use.

The device of the first aspect is preferably adapted to permit both the storage of a sclerosant fluid and the production of a sclerosing microfoam. In a particularly preferred embodiment of the first aspect of the present invention there is provided a device for producing a microfoam suitable for use in scleropathy of blood vessels, particularly veins. Preferably mixing of gas and aqueous sclerosant occurs inside the aerosol valve at the mouth of the expandable inner container.

Preferably the device of the first aspect comprises a canister, an expandable inner container affixed to the outer opening of the canister or to the aerosol valve housing above the gas-entry ports of the valve, a solution of the sclerosing agent in a physiologically acceptable solvent, a pathway with one or more outlet orifices by which the solution may pass from the expandable inner container to the exterior of the device through said one or more outlet orifices and a mechanism by which the pathway from the inner container to the exterior can be opened or closed such that, when the container is pressurised and the pathway is open, a gas-solution mixture will be forced along the pathway and through the one or more outlet orifices, said canister incorporating an inlet for the admission of a pressurised source of physiologically acceptable gas that is dispersible in blood; the gas being in contact with the solution on activation of the mechanism such as to produce the gas-solution mixture; said pathway to the exterior of the canister including one or more foaming elements; and the blood-dispersible gas is stored in a container provided with engaging means for the canister holding the aqueous sclerosant liquid.

In a second aspect of the present invention there is provided a device for producing a microfoam suitable for use in scleropathy of blood vessels, particularly veins, comprising a comprising an aerosol valve housing mounted on a canister, an expandable inner container affixed to the outer opening of the canister or to the aerosol valve housing, whereby the introduction of pressurised gas through the aerosol valve causes the expandable inner container to inflate to accommodate the pressurised gas, a pathway with one or more outlet orifices by which the solution may pass from the inner container to the exterior of the device through said one or more outlet orifices and a mechanism by which the pathway from the inner to the exterior can be opened or closed such that, when the container is pressurised and the pathway is open, gas-solution mixture will be forced along the pathway and expelled through the one or more outlet orifices;

said canister incorporating an inlet for the admission of a pressurised source of physiologically acceptable gas that is dispersible in blood; the gas being in contact with the solution on activation of the mechanism such as to produce a gas-solution mixture;

said pathway to the exterior of the device including one or more foaming elements.

The foaming elements may be mounted either inside the canister, as disclosed in WO 00/72821-A1, or on the exterior of the canister, as disclosed in co-pending application WO 02/41872-A1.

Preferably the expandable inner container contains a solution of the sclerosing agent.

Preferably the solution of the sclerosing agent is mixed with physiologically acceptable gas in a predetermined proportion.

As described above the device of the invention comprises an expandable inner container, which holds the aqueous sclerosant. Preferably this container comprises a flexible, expandable substantially gas-impermeable material, usually in the form of a pleated bag. The expandable inner container is affixed to the outer opening of the canister, preferably either to a valve positioned therein or trapped between the canister curl and the valve-mounting cup. Alternatively the expandable inner container is attached internally to the aerosol valve housing. The inner container can be made from a number of different materials, preferably strong flexible materials such as plastics, metal foils or metallised plastic foils. Metal foil is particularly preferred to maintain sterility, provide mechanical strength and prevent gas ingress during storage. Suitable plastics include selected nylons, PET or polypropylene. The expandable inner container can be made using a number of different techniques including blow moulded plastics and welded laminate constructs comprising various plastic and metal layers. When the device is used to produce a sclerosing foam, the expandable inner container will be subjected to a few bar internal pressure produced by the introduction of the physiologically acceptable gas. The expandable inner container expands to fill the volume of the canister, and is restricted from further expansion by the outer canister walls. The expandable inner container may therefore be a relatively thin-walled bag, as long as it is of a larger internal volume than the outer, constraining canister, thus avoiding the possibility of the expandable inner container bursting under the internal pressure produced by the introduction of the pressurised gas.

The canister may contain an inert gas or atmospheric gas which surrounds the expandable inner container. If atmospheric gas is to be used the expandable inner container preferably comprises a material such as metal or metallised foil to prevent ingress of the gas. Introduction of the physiologically acceptable blood-dispersible gas into the inner container during foam production causes it to expand inside the canister. Any gas inside the canister may exert pressure on the expandable inner container, which could effectively limit its capacity. Therefore, it is preferable to include a mechanism in the device to reduce the pressure inside the canister and permit full expansion of the expandable inner container. Preferably this mechanism comprises a vent in the canister; preferably this vent is sealed during storage and is opened, for example by means of a tear strip or pressure sensitive seal, prior to use. Preferably the vent is located in the base of the canister. Alternatively, the canister may contain a vent hole, for example at its base, which is always open. Another option is to have no vent hole and accept a slightly smaller volume of the inner container when expanded, owing to the trapped gas between expandable inner container and canister wall.

Preferably the canister and inner expandable container are sized such that the device can contain sufficient gas and solution to form up to 500 ml of microfoam, more preferably from 1 ml up to 200 ml and most preferably from 10 to 60 ml of microfoam. Particularly the amount of gas under pressure in such a device should be sufficient to produce enough foam to treat, i.e. fill at least one varicosed human saphenous vein. The most preferred canister device is disposable after use, or cannot be reused once opened such as to avoid problems of maintaining sterility.

The gas pressure employed will be dependent upon materials being used and their configuration, but conveniently will be 0.01 to 9 bar over atmospheric, more preferably 0.1-3 bar over atmospheric, and still more preferably 1.5-2.5 bar over atmospheric pressure.

It may be most convenient to produce a device in which the expandable container is housed inside a canister, as an expandable inner container. However, the device of the present invention is not limited to this configuration, as the expandable container alone may, when constructed of strong gas impermeable materials, such as metal foils, be sufficient to maintain sterility, provide mechanical strength and prevent gas ingress into the sclerosant solution during storage.

Therefore, in a third aspect of the present invention there is provided a device containing sclerosant liquid for use in the treatment of blood vessels comprising an aerosol valve housing and an expandable container in which the sclerosant fluid is contained, wherein the expandable container is affixed to the aerosol valve housing, whereby the introduction of pressurised gas through the aerosol valve causes the expandable container to inflate to accommodate the pressurised gas.

In a fourth aspect of the present invention there is provided a device for producing a microfoam suitable for use in scleropathy of blood vessels, in the form of a kit comprising:
(a) a device comprising a comprising an aerosol valve housing mounted on a canister having an expandable inner container containing an aqueous solution of the sclerosing agent affixed to the outer opening of the canister, or to the aerosol valve housing, whereby the introduction of pressurised gas through the aerosol valve causes the expandable inner container to inflate to accommodate the pressurised gas; a pathway with one or more outlet orifices by which the solution may pass from the pressurisable chamber to the exterior of the device through said one or more outlet orifices; and a mechanism by which the pathway from the chamber to the exterior can be opened or closed such that, when the container is pressurised and the pathway is open, a gas-solution mixture will be forced along the pathway and through the one or more outlet orifices; and
(b) a pressurised container containing a physiologically acceptable blood-dispersible gas;
said canister incorporating an inlet for the admission of blood-dispersible gas; the gas being in contact with the solution on activation of the mechanism such as to produce the gas-solution mixture.

The aqueous solution of the sclerosing agent may further include a physiologically acceptable buffer.

Either inside the inner container disposed in the pathway to the valve, or on the downstream side of the valve, is provided a foaming element or elements having the one or more passages mounted such that the gas-liquid mixture, i.e. dispersion of bubbles in liquid, aerosol or macrofoam, passes through the passage or passages and is caused to foam. This element may conveniently be located outside the canister on the stem valve outlet from the canister. Conveniently, depression of the foaming elements in their housing operates the valve. Alternatively the foaming elements are within the canister mounted above the gas-liquid interface, and above the gas path entry ports to the mixing valve.

The foaming element(s) may comprise one or more passages of cross sectional dimension, preferably diameter, 0.1 μm to 30 μm, through which the solution and gas mixture is passed to reach the exterior of the device, said passing of said mixture through the passages forming a microfoam of from 0.07 to 0.19 g/ml density and of half-life at least 2 minutes.

Preferred forms of the one or more elements defining the multiple passages for use in the device of the present invention are meshes, screens, sinters or other microporous membranes. Thus one or more meshes or perforated screens or sinters will be provided, with some preferred forms employing a series of such elements arranged in parallel with their major surfaces perpendicular to the path of solution/gas expulsion.

In a fifth aspect of the present invention there is provided a device comprising a canister containing a storage gas and a pressurisable inner container containing a sclerosant liquid for use in the treatment of blood vessels, wherein the sclerosant liquid and storage gas are maintained in isolation through separation on opposite sides of a movable barrier.

The storage gas may be an inert gas or atmospheric gas adjacent to or surrounding the pressurisable inner container. If atmospheric gas is to be used the expandable inner container preferably comprises a material such as metal or metallised foil to prevent ingress of the gas.

Preferably the device of the fifth aspect is configured such that the sclerosant liquid contained therein may be mixed with a pressurised gas comprising a physiologically acceptable blood dispersible gas to produce a sclerosing foam. Preferably the physiologically acceptable blood dispersible gas is stored in a separate container prior to use.

Different types of barrier vessels may be used in the device of the fifth aspect. In a typical piston-type barrier vessel the barrier is a piston-like component that is mounted in the container in sliding relation to the inside surface of the container. The product to be dispensed is disposed on the valve side of the piston and the propellant, which generates pressure within the container, is on the opposite side of the piston. An example of a piston-type barrier pack is described in U.S. Pat. No. 3,756,476 (Bonduris/Colgate-Palmolive Company). However, as will be apparent to those skilled in the art, this type of device requires adaptation for use in the present invention, for example, packaging of the solution in a bag-on-valve pouch with integral diptube, the inclusion of an expandable inner container or the use of the piston to alter the volume of the final pressurised compartment.

In a second variant of an aerosol barrier vessel, a flexible collapsible inner container is affixed within an outer canister opening either to the aerosol discharge valve or to the bead of the canister opening, as in the device of the first aspect.

In a third variant the barrier vessel is an unfolding cup-shaped barrier wherein the barrier has an outer wall terminating in a sealing flange, said outer wall being disposed contiguous to the inner wall of the container. This type of barrier vessel is illustrated in WO 96/02439-A1 (Abplanalp).

The sclerosant liquid utilised in the device and method of the invention may be any of those discussed in co-pending application WO 02/41872-A1 and WO 00/72821-A1. Preferably the sclerosant liquid is aqueous polidocanol. More preferably the sclerosing agent is a solution of polidocanol or sodium tetradecyl sulfate in an aqueous carrier, e.g. water, particularly in a saline. More preferably the solution is from 0.25 to 5% v/v polidocanol, preferably in sterile water or a physiologically acceptable saline, e.g. in 0.5 to 2% v/v saline. Concentration of sclerosant in the solution will be advantageously increased for certain abnormalities such as Klippel-Trenaunay syndrome.

The sclerosant may also contain additional components, such as stabilising agents, e.g. foam stabilising agents, e.g. such as glycerol. Further components may include alcohols such as ethanol. Inclusion of a few percent of ethanol is thought to solubilise low-molecular-weight oligomers of polidocanol.

Most preferably the concentration of sclerosant in the aqueous liquid is a 0.25-2% vol/vol solution, preferably of polidocanol, in water or saline. The water or saline also may contain 2-5% vol/vol physiologically acceptable alcohol, e.g. ethanol. The polidocanol solution is preferably phosphate buffered. Preferably this buffering is such that a pH neutral foam is produced.

The sclerosant liquid may be stored at atmospheric pressure (or just above) before the blood-dispersible gas is introduced. The sclerosant liquid may be stored in the presence of an inert gas or mixture of inert gases. "Inert gas", as used in this specification, refers to one which is unlikely to react with the sclerosant liquid so as to change its chemical nature. Suitable inert gases include carbon dioxide, helium, neon, argon, and nitrogen. Carbon dioxide is most preferred, as it is physiologically acceptable, as part of the final gas mix in the microfoam. Helium is next best, as it is of small molecular weight, and diffuses through alveolar blood vessel walls very quickly.

Advantageously, a vacuum can be drawn on the expandable inner container prior to or after filling with sclerosant. This reduces to a minimum the amount of gas, particularly undesirable gases, such as nitrogen or carbon dioxide, which may affect the sclerosant during storage or the composition of the resulting foam. Alternatively, a small amount of inert gas may be filled into the bag after charging with polidocanol solution, to keep polidocanol solution away from the valve components, though this would require the canister to be stored upright at all times.

The invention allows the physiologically acceptable blood-dispersible gas to be introduced into the device holding the aqueous sclerosant liquid immediately before the mixture of blood-dispersible gas and sclerosant liquid is released. This would conveniently be performed on the same day as the foam is to be used in scleropathy of blood vessels, or within a twenty-four period prior to the foam being so used. The foam does not have to be used immediately; moreover, if the device holding the aqueous sclerosant liquid is inadvertently shaken while the blood-dispersible gas is introduced, it can be desirable to leave it for five or so minutes to allow the contents to settle. Thus the formation of an undesirable macrofoam within the bag is avoided.

The device with the expandable inner container containing the solution of the sclerosing agent and the container containing the blood-dispersible gas are preferably placed in a sealed package, or otherwise sold as a single unit. This would normally be intended for a single treatment, and discarded after use.

The source of blood-dispersible gas may remain in place while the foam is being dispensed, if the gas inlet and foam outlet are separate. However, preferably the source of the blood-dispersible gas is removed before the mixture of blood-dispersible gas and sclerosant liquid is released, having pressurised the mixture to a pre-determined level. This allows the inlet for the admission of physiologically acceptable gas to be used as the outlet for dispensing of the metered mixture of blood-dispersible gas and sclerosant liquid.

The blood-dispersible gas may be stored in a container provided with engaging means as disclosed in the co-pending application WO 02/41872-A1. A connector may also be incorporated, as disclosed in the same application.

It is preferred that any elements in the devices according to the invention which have a critical dimension, and which are likely to be exposed to an aqueous solution for more than a few minutes, are made of a material that does not change dimension when exposed to aqueous material. Thus such elements preferably should not be of a water-swellable material such as Nylon 6,6, but of a polyolefin such as polypropylene or polyethylene. On the other hand, Nylon 6,6 is ideal for elements where exposure to aqueous solution is so short that swelling is unlikely, such as the element defining the passages of 0.1 μm-30 μm dimension. Nylon 6,3 may also be used.

For the purpose of this application terms have the following definitions. Physiologically acceptable blood dispersible gas is a gas that is capable of being substantially completely dissolved in or absorbed by blood. A sclerosant liquid is a liquid that is capable of sclerosing blood vessels when injected into the vessel lumen. Scleropathy or sclerotherapy relates to the treatment of blood vessels by injection of a sclerosing agent to eliminate them. An aerosol is a dispersion of liquid in gas. A major proportion of a gas is over 50% volume/volume. A minor proportion of a gas is under 50% volume/volume. A minor amount of one liquid in another liquid is under 50% of the total volume. Half-life of a microfoam is the time taken for half the liquid in the microfoam to revert to unfoamed liquid phase, under the influence of gravity, and at a defined temperature.

The mixture of blood-dispersible gas and sclerosant liquid is preferably pressurised to a pre-determined level. Preferred pressures are in the range 800 mbar to 4.5 bar gauge (1.8 bar to 5.5 bar absolute). Pressures in the range of 1 bar to 2.6 bar gauge have been found to be particularly effective—over this range of pressures, there is very little change in either the density or the half-life of the resulting foam as the canister empties.

Preferably the microfoam is such that 50% or more by number of its gas bubbles of 25 μm diameter and over are no more than 200 μm diameter.

Preferably the gas/liquid ratio in the mix is controlled such that the density of the microfoam is 0.09 g/ml to 0.19 g/ml, more preferably 0.10 g/ml to 0.16 g/ml.

Preferably the microfoam has a half-life of at least 2 minutes, more preferably at least 3 minutes. The half-life may be as high as 1 or 2 hours or more, but is preferably less than 60 minutes, more preferably less than 15 minutes and most preferably less than 10 minutes.

Half-life is conveniently measured by filling a vessel with a known volume and weight of foam and allowing liquid from this to drain into a graduated vessel, the amount drained in a given time allowing calculation of half-life i.e. of conversion of microfoam back into its component liquid and gas phases. This is preferably carried out at standard temperature and pressure, but in practice ambient clinic or laboratory conditions will suffice.

The ratio of gas to liquid used in the final mixture is important in order to control the structure of the microfoam produced such that its stability is optimised for the procedure and the circumstances in which it is being carried out. For optimum foams it is preferred to mix 1 volume of sclerosant liquid with from approximately 4 to 10 volumes (STP), more preferably 6 to 8 volumes (STP), of gas.

The gas pressure employed will be dependent upon materials being used and their configuration, but conveniently will be 0.01 to 9 bar over atmospheric, more preferably 0.1-3 bar over atmospheric, and still more preferably 1.5-2.5 bar over atmospheric pressure.

Suitable pressures before the mixture of blood-dispersible gas and sclerosant liquid is released are typically in the range 0.01 to 9 bar over atmosphere. For use of meshes, e.g. one to eight meshes arranged in series, having apertures of 1-50 μm diameter, 0.8 to 4.5 bar over atmospheric pressure will, inter alia, be suitable. For use of three to five meshes of 20 μm aperture it is found that 1.5-1.7 bar over atmospheric is sufficient to produce a good foam. A pressure of 2-2.5 bar over atmospheric may advantageously be used. For a 1 μm pore size membrane, a pressure of 5 bar or more over atmospheric pressure is preferred.

In one preferred form of the invention the passages are in the form of a membrane, e.g. of polymer such as polytetrafluoroethylene, wherein the membrane is formed of randomly connected fibres and has a rated effective pore size which may be many times smaller than its apparent pore size. A particularly suitable form of this is a biaxially oriented PTFE film provided by Tetratec™ USA under the trade mark Tetratex™, standard ratings being 0.1 to 10 μm porosity. Preferred pore sizes for the present method and devices are 3 to 7 μm. This material may be laminated with a porous backing material to give it strength and has the advantage that one or two such meshes may be sufficient to produce a foam that meets the use requirements set out above with regard to stability.

The present invention also provides for methods of producing a sclerosing foam, preferably a microfoam, using the devices of the invention.

Thus in a sixth aspect of the present invention there is provided a method for producing a sclerosing foam comprising introducing a pressurised physiologically acceptable blood dispersible gas into an expandable container in which sclerosant fluid is contained, wherein the introduction of said gas causes the container to inflate; and releasing the resulting gas-sclerosant mixture from the container to form a sclerosing foam.

Preferably the pressurised gas is introduced into an expandable container that is affixed to the outer opening of an aerosol canister or to an aerosol valve housing.

Preferably the pressurised gas is introduced through the aerosol valve.

Preferably mixing of the gas-sclerosant mixture occurs inside an aerosol valve at the mouth of the expandable container.

Preferably the pressurised gas is stored in a separate container prior to use.

Preferably the gas-sclerosant mixture is released through a foaming element or elements such that the gas-sclerosant mixture passes through the passage or passages in the foaming element and is caused to foam.

In a seventh aspect of the invention there is provided a method for producing a microfoam suitable for use in scleropathy of blood vessels comprising introducing pressurised physiologically acceptable blood dispersible gas into a device containing sclerosant solution contained in an expandable inner container, wherein the gas is introduced into the container through an aerosol valve causing the container to inflate; and passing the resulting pressurised gas-solution mixture from the inner container through a pathway to the exterior of the device, the pathway including one or more foaming elements, such that a sclerosing microfoam is produced.

The present invention will now be described further by way of illustration only by reference to the following Figures and Examples. Further embodiments falling within the scope of the invention will occur to those skilled in the art in the light of these.

BRIEF DESCRIPTION OF THE DRAWINGS

FIG. 6 shows a cross-sectional view of a device comprising a container provided with engaging means and a mesh stack shuttle according to the invention, as disclosed in the co-pending application WO 02/41872-A1 and further described in Example 3 below.

EXAMPLES

Figure 1:
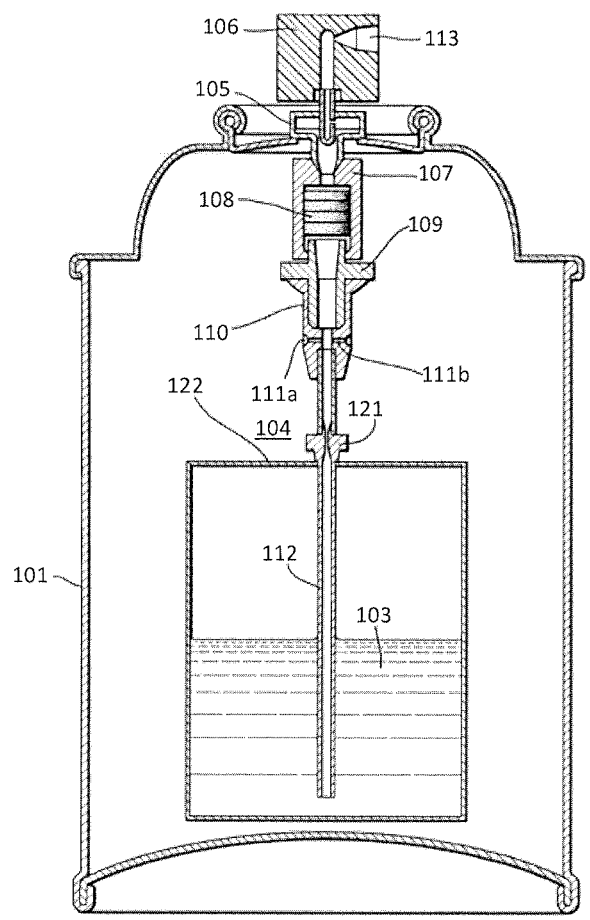
FIG. 1 shows a cross-sectional view of a prior art canister device incorporating a bag-on-valve reservoir for the sclerosant with the gas being in the outer chamber, as disclosed in WO 00/72821-A1.

A prior art canister device incorporating a bag-on-valve reservoir for the sclerosant with the gas being in the outer chamber as disclosed in WO 00/72821-A1 is shown in FIG. 1. A polidocanol sclerosing solution (103) is enclosed in a foil bag (122), comprising an aluminum foil/plastics laminate (Coster Aerosols Ltd., Stevenage, UK) sealed in gas tight fashion to a dip-tube (112). At the top end of the dip-tube is a one-way duck-bill valve that serves to prevent contact of polidocanol with the contents of the dip-tube (112) and chamber (104) until the valve (105) is operated. On said operation the valve (121) opens and polidocanol solution (103) is caused to rise up the dip-tube (112), whereby it becomes mixed with the gas mixture entering through holes (111a, 111b).

Example 1

"Bag-in-can" Device

Figure 2:
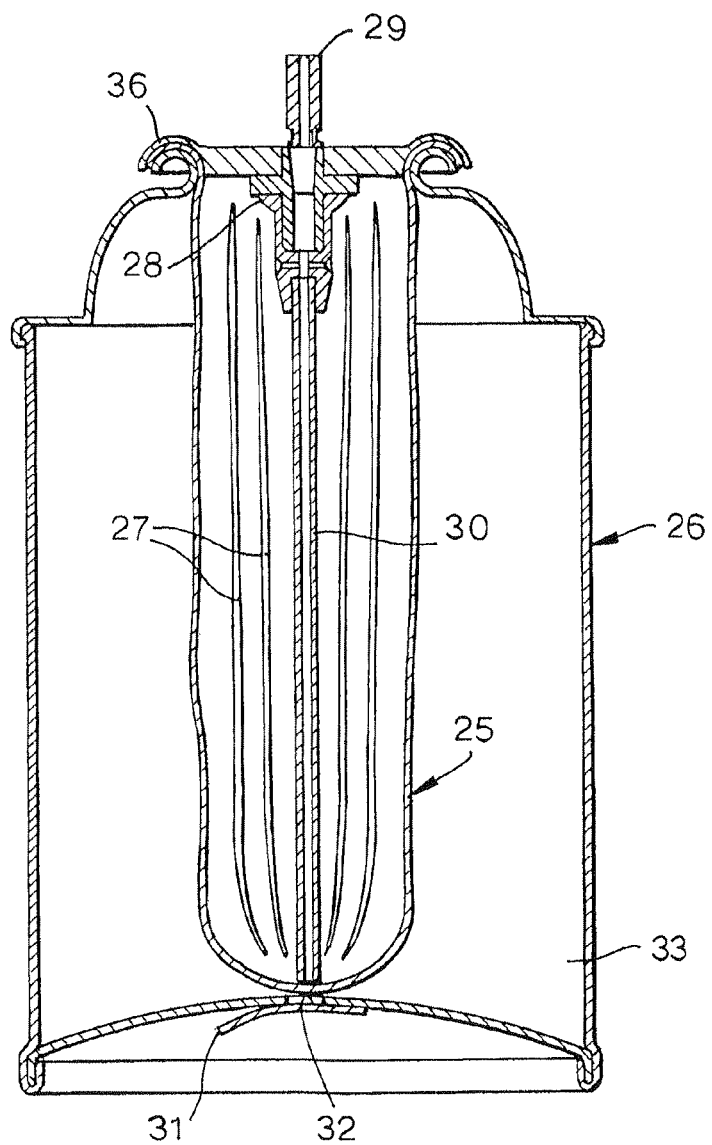
FIG. 2 shows a cross-sectional view of an empty "bag-in-can" device according to the invention, as further described in Example 1 below.

A first embodiment of the present invention is shown in FIG. 2. The device uses a standard bag-in-can construction of the type supplied by US Can Corporation of Lombard, Ill., or Crown Cork & Seal Company Inc. of Philadelphia, Pa. The bag (25), typically composed of blow moulded nylon 6,6 or HDPE, but not limited to these polymers, and of an inflated size ideally equal to or greater than the internal volume of the canister, is inserted into the can (26) through the open mouth of the canister. A number of axial pleats (27) in the bag wall (25) aid in easy insertion of the bag through the open mouth of the can. A mixing valve (28) (e.g. Ecosol™ type, Precision Valve, Peterborough, UK) is crimped onto the can, trapping the mouth of the bag in the valve crimp (36) and effecting a seal.

A vacuum pump is attached to the stem valve outlet (29) of the sealed can, the valve is depressed to open a pathway to the bag interior, and a vacuum drawn inside the bag to a level between 0.5 bar absolute and 0.1 bar absolute. This procedure minimises the gas volume inside the bag.

A sclerosant solution of, for example, polidocanol is then filled into the evacuated bag via the stem valve (28) and dip tube (30). An optional tab (31) on the base of the can may be added to cover and seal the small hole (32) in the base of the can, after optionally filling the space (33) between the bag and the can with an inert gas to eliminate the possibility of atmospheric oxygen diffusing through the bag wall and oxidising the liquid sclerosant stored inside the bag, as common engineering plastics of the type used in blow moulding of bags tend to have fairly high oxygen transmission rates.

The canister can be charged with oxygen, at a later time just prior to use, through the stem valve and dip tube, to a pressure between 1.8 bar absolute and 4.5 bar absolute to pressurise the bag and allow the production of sclerosant foam by the methods described in co-pending application WO 02/41872-A1 and further described in Example 3 below.

Figure 3:
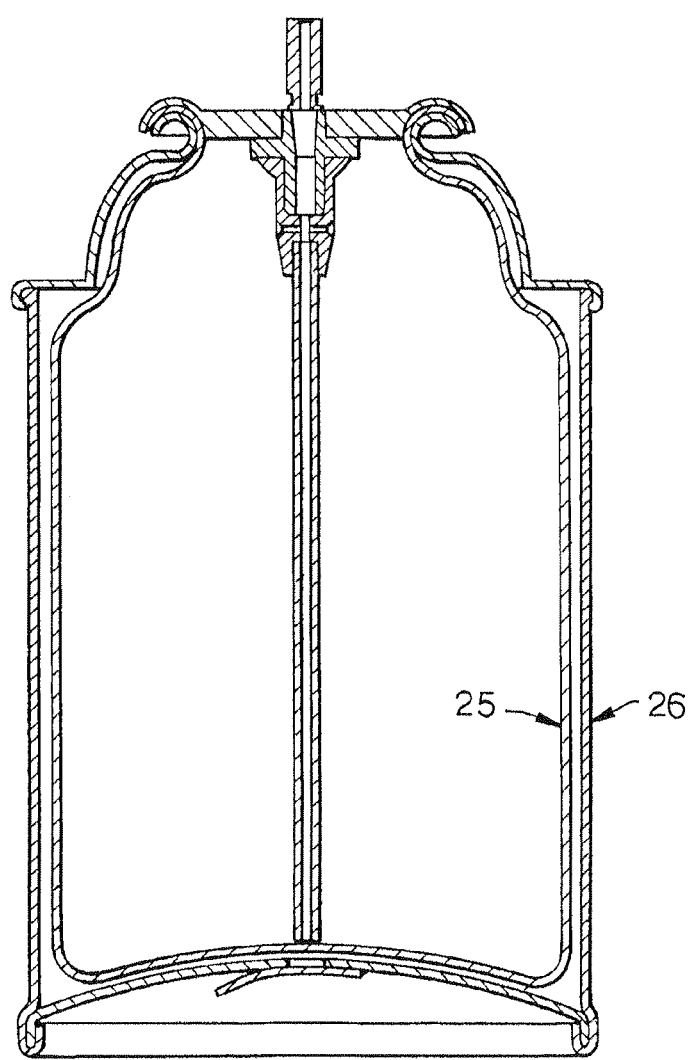
FIG. 3 shows a cross-sectional view of a full "bag-in-can" device according to the invention, as further described in Example 1 below.

The charged canister is shown in FIG. 3 (the sclerosant solution in the bag is not shown). The pressurised bag (25) has expanded to fill the internal volume of the can (26). It is not essential to have the hole (32) in the base of the can, as the system will work without this, but if not present the bag will not be able to expand to the full internal volume of the canister, as it will compress the gas in between the bag and the canister.

Example 2

"Bag-on-Valve" Device

Figure 4:
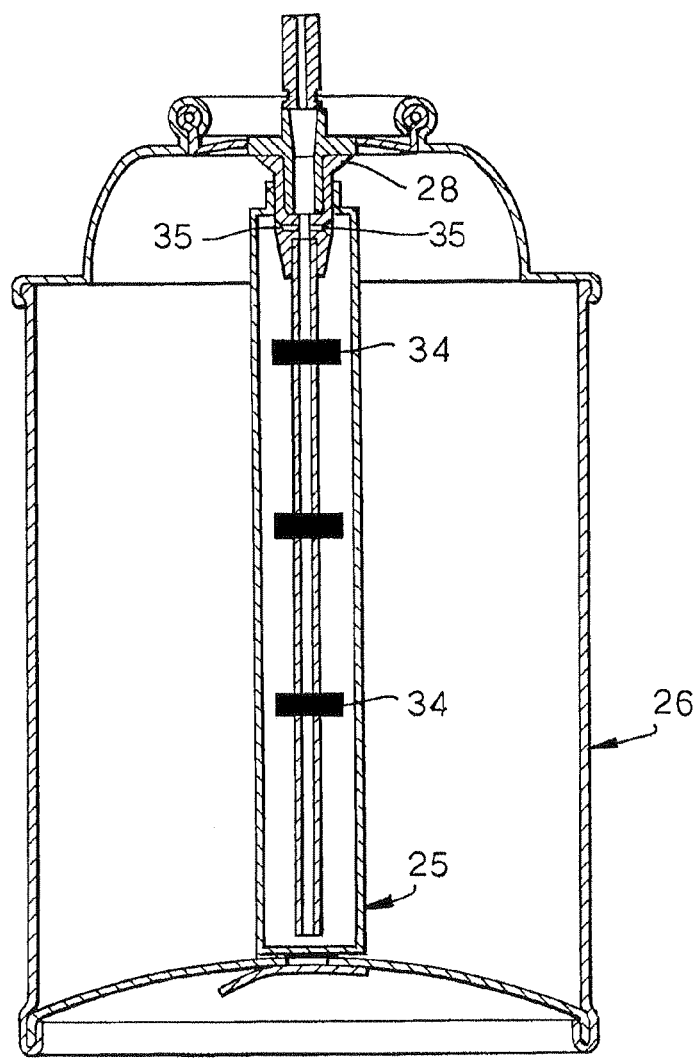
FIG. 4 shows a cross-sectional view of an empty "bag-on-valve" device according to the invention, as further described in Example 2 below.

A further embodiment of the present invention is shown in FIG. 4, which is broadly similar in operation to Example 1, though incorporating a "bag-on-valve" device. FIG. 4 shows the device in its unfilled state. Such bags are normally constructed from a tri-layer laminate comprising a heat sealable material on the inner surface (PVdC or similar), an aluminium foil as the centre layer, and a tough plastic for the outer layer (PET, Nylon 6,6 or similar). The bags are normally supplied coiled or furled around the central long axis by companies such as Coster Aerosols Ltd., Stevenage, UK, and normally contain a dip tube (30). To keep them tightly furled, it is normal practice to employ a number of adhesive tape tabs (34) that are based on a weak paper backing. When the bag (25) is subsequently inflated, these tabs tear and allow the bag to fill almost the entire volume of the canister (26). In this example, it is critical that the weld between the bag and the valve (28) is above the valve gas slots (35), so that the gas mixed with the liquid to create a sclerosing foam is taken from the interior of the bag. The size of the bag is chosen to have the same or greater internal volume than the canister. In this way, the pressure inside the bag, once charged, will be supported mainly by the canister walls.

Figure 5:
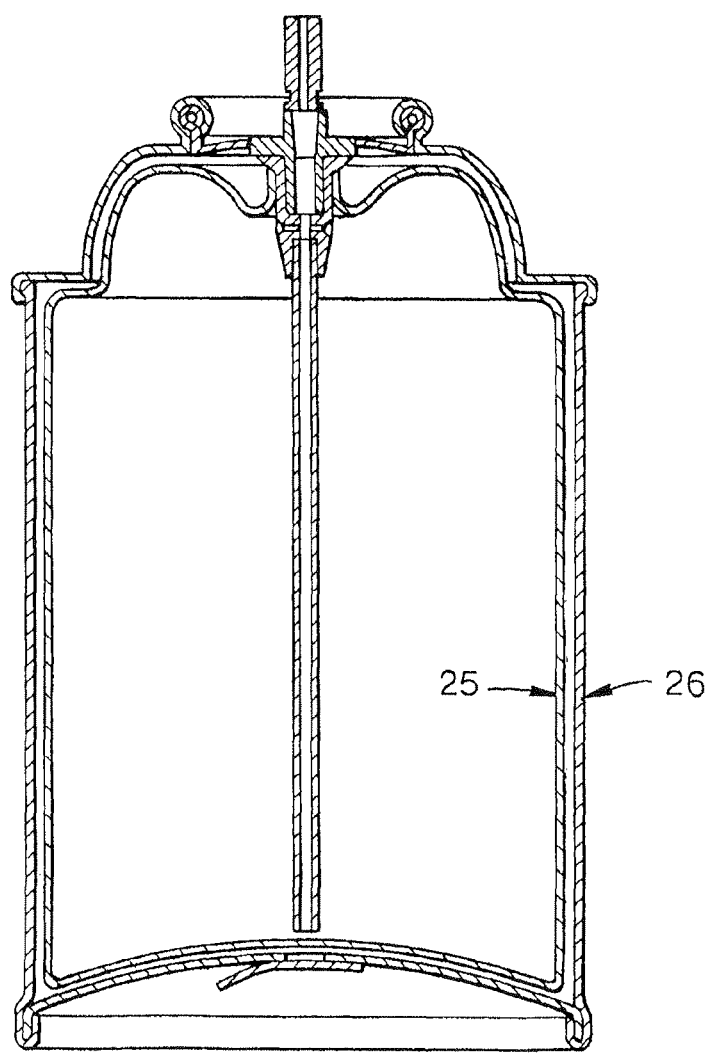
FIG. 5 shows a cross-sectional view of a full "bag-on-valve" device according to the invention, as further described in Example 2 below.

The procedure for filling and pressurising the internal volume of the bag-on-valve is the same as described in Example 1, except that the vacuum stage may be optionally eliminated. The filled pressurised bag-on-valve is shown in FIG. 5 (the sclerosant solution in the bag is not shown). The bag (25) has expanded to fill the internal volume of the canister (26).

Example 3

Container with Engaging Means and Mesh Stack Shuttle

A device comprising a container provided with engaging means and a mesh stack shuttle according to the invention, as disclosed in the co-pending application WO 02/41872-A1, is shown in FIG. 6. The device comprises a container (1) for an aqueous sclerosant liquid, a container (2) for a physiologically acceptable blood-dispersible gas and an engaging means comprising a connector (3).

The container (1) for the aqueous sclerosant liquid is pressurised to a level of 0.5 bar absolute. The container (2) for a physiologically acceptable blood-dispersible gas is charged with pure oxygen gas at 5.8 bar absolute pressure. Container (2) is used to pressurise the container (1) for the aqueous sclerosant liquid just before the microfoam is required, and is then discarded. The two containers will thus be referred to hereinafter as the PD [polidocanol] can (1) and the $O_2$ can (2). In this example each of the containers (1,2) has approximately 300 ml internal volume, and are rigid aerosol canisters of fixed internal volume.

Each of the cans (1, 2) is provided with a snap-fit mounting (4, 5). These may be made as identical mouldings. The snap-fit parts (4, 5) engage the crimped-on mounting cup (6, 7) of each can (1, 2) with high frictional force. The connector is made in two halves (8, 9), and the high frictional force allows the user to grip the two connected cans (1, 2) and rotate the connector halves (8, 9) relative to each other without slippage between connector (3) and cans. Each of these can mountings (6, 7) has snap-fit holes (10, 11) for engaging mating prongs (12, 13) which are on the appropriate surfaces of the two halves (8, 9) of the connector.

The connector (3) is an assembly comprising a number of injection mouldings. The two halves (8, 9) of the connector are in the form of cam track sleeves which fit together as two concentric tubes. These tubes are linked by proud pins (14) on one half that engage sunken cam tracks (15) on the other half. The cam tracks have three detented stop positions. The first of these detents is the stop position for storage. An extra security on this detent is given by placing a removable collar (16) in a gap between the end of one sleeve and the other. Until this collar (16) is removed it is not possible to rotate the sleeves past the first detent position. This ensures against accidental actuation of the connector.

A further element of security is given by providing a tamper-evident label across the join between the cam track sleeve (9) and the removable collar (16).

The cam track sleeves (8, 9) are injection moulded from ABS as separate items, and are later assembled so that they engage one another on the first stop of the detented cam track. The assembled sleeves are snap-fitted as a unit onto the $O_2$ can (2) mounting plate (5) via four locating prongs. The security collar and tamper-evident label are added at this point to make an $O_2$ can subassembly.

The connector (3) includes in its interior a series of foaming elements comprising a mesh stack shuttle (17) on the connector half (8) adjacent to the PD can (1). The mesh stack shuttle (17) is comprised of four injection moulded disk filters with mesh hole size of 20 microns and an open area of approx. 10-15%. These are pre-assembled within a casing tube (18). The end fittings of the stack (17) are designed to give gas-tight face and/or rim seals against the stem valves (19, 20) of the two cans (1, 2) to ensure sterility of gas transfer between the two cans.

The mesh stack shuttle (17) is assembled onto the PD can valve (19) by push-fitting the components together in a sterile environment.

The PD can (1) and attached shuttle (17) are offered up to the connector (3) and the attached $O_2$ can (2), and a sliding fit made to allow snap-fitting of the four locating prongs (12) on the PD can side of the connector (3) into the mating holes (10) in the mounting plate (4) on the PD can (1). This completes the assembly of the system. In this state, there is around 2 mm of clearance between the stem valve (20) of the $O_2$ can (2) and the point at which it will form a seal against a female luer outlet from the stack.

When the tamper-evident sleeve and security collar (16) are removed, it is possible to grasp the two cans (1, 2) and rotate one half of the connector (3) against the other half to engage and open the can valve (19,20).

As the rotation of the connector (3) continues to its second detent position, the valves (19, 20) open fully. The gas flow from the $O_2$ can (2) to the PD can (2) is restricted by a small outlet hole (21) in the stem valve (20). It takes about 30 seconds at the second detent position for the gas pressure to (almost) equilibrate between the two cans to a level of 3.15 bar±0.15 bar.

After the 30 second wait at the second detent position, the connector (3) is rotated further to the third detent position by the user. At this position, the two cans (1, 2) can be separated, leaving the PD can (1) with half (8) of the connector and the shuttle assembly (17) captive between the connector and the PD can. The $O_2$ can (2) is discarded at this point.

A standard 1 inch diameter aerosol valve (19) (Precision Valve, Peterborough, UK) is crimped into the top of the PD can (1) before or after sterile filling with the solution and is activatable by depressing the mesh stack shuttle (17), which functions as an aerosol valve actuator mechanism, to release the contents via an outlet nozzle (22) sized to engage a luer fitting of a syringe or multi-way connector (not shown).

The invention claimed is:

1. A device containing sclerosant liquid for use in the treatment of blood vessels comprising an aerosol valve housing comprising gas-entry ports, wherein the aerosol valve housing is mounted on a canister having an expandable inner container in which the sclerosant fluid is contained, wherein the expandable inner container is affixed to the outer opening of the canister or to the aerosol valve housing above the valve gas-entry ports so that gas taken from the interior of the expandable inner container can mix with the sclerosant liquid to create a micro foam, whereby the introduction of pressurised gas through the aerosol valve causes the expandable inner container to inflate to accommodate the pressurised gas, wherein the device includes a vent in the canister that is sealed during storage and is opened prior to use to reduce the pressure inside the canister and permit full expansion of the expandable inner container.

2. A device according to claim 1 wherein the sclerosant liquid contained therein may be mixed with a pressurised gas comprising a physiologically acceptable blood dispersible gas to produce a sclerosing foam.

3. A device according to claim 1 wherein the physiologically acceptable blood dispersible gas is stored in a separate container prior to use.

4. A device according to claim 1 wherein mixing of gas and aqueous sclerosant occurs inside the aerosol valve at the mouth of the expandable inner container.

5. A device according to claim 1 comprising a pathway with one or more outlet orifices by which the sclerosing liquid may pass from the expandable inner container to the exterior of the device through said one or more outlet orifices and a mechanism by which the pathway from the inner container to the exterior can be opened or closed such that, when the container is pressurised and the pathway is open, the pressurised gas contacts the sclerosant liquid within the pathway to produce a gas-solution mixture; the gas-solution mixture is forced along the pathway and through the one or more outlet orifices, said pathway to the exterior of the canister including one or more foaming elements; and the blood-dispersible gas is stored in a container provided with engaging means for the canister holding the aqueous sclerosant liquid.

6. A device for producing a microfoam suitable for use in scleropathy of blood vessels, comprising an aerosol valve housing comprising gas-entry ports, wherein the aerosol valve housing is mounted on a canister, an expandable inner container affixed to the outer opening of the canister or to the aerosol valve housing above the valve gas-entry ports so that gas taken from the interior of the expandable inner container can mix with the sclerosant liquid to create the microfoam, whereby the introduction of pressurised gas through the aerosol valve causes the expandable inner container to inflate to accommodate the pressurised gas, a pathway with one or more outlet orifices by which the solution may pass from the inner container to the exterior of the device through said one or more outlet orifices and a mechanism by which the pathway from the inner to the exterior can be opened or closed such that, when the container is pressurised and the pathway is open, a gas-solution mixture will be forced along the pathway and expelled through the one or more outlet orifices;

said canister incorporating an inlet for the admission of a pressurised source of physiologically acceptable gas that is dispersible in blood; the gas being in contact with the solution on activation of the mechanism such as to produce the gas-solution mixture;

said pathway to the exterior of the device including one or more foaming elements;

wherein the device includes a vent in the canister that is sealed during storage and is opened prior to use to reduce the pressure inside the canister and permit full expansion of the expandable inner container.

7. A device according to claim 6 wherein the expandable inner container contains a solution of the sclerosing agent.

8. A device according to claim 7 wherein the solution of the sclerosing agent is mixed with physiologically acceptable gas in a predetermined proportion.

9. A device according to claim 1 wherein the expandable inner container comprises a flexible, expandable substantially gas-impermeable material.

10. A device according to claim 8 wherein the expandable inner container is in the form of a pleated bag.

11. A device according to claim 10 wherein the expandable inner container comprises metal or metallised foil.

12. A device for producing a microfoam suitable for use in scleropathy of blood vessels, in the form of a kit comprising:
(a) a device according to claim 1; and
(b) a pressurised container containing a physiologically acceptable blood-dispersible gas;
said canister incorporating an inlet for the admission of blood-dispersible gas; the gas being in contact with the solution on activation of the mechanism such as to produce the gas-solution mixture.

13. A device according to claim 12 wherein a foaming element or elements is provided having one or more passages mounted such that the gas-liquid mixture passes through the passage or passages and is caused to foam.

14. A device according to claim 13 wherein the foaming element(s) comprises one or more passages of cross sectional dimension 0.1 µm to 30 µm, through which the gas-liquid mixture is passed to reach the exterior of the device, said passing of said mixture through the passages forming a microfoam of from 0.07 to 0.19 g/ml density and of half-life at least 2 minutes.

15. A device according to claim 1 wherein the sclerosant liquid is a solution of polidocanol or sodium tetradecyl sulfate in an aqueous carrier.

16. A device containing sclerosant liquid for use in the treatment of blood vessels comprising an aerosol valve housing comprising gas-entry ports and an expandable container in which the sclerosant fluid is contained, wherein the expandable container is affixed to the aerosol valve housing above the valve gas-entry ports so that gas taken from the interior of the expandable inner container can mix with the sclerosant liquid to create a microfoam, whereby the introduction of pressurised gas through the aerosol valve causes the expandable container to inflate to accommodate the pressurised gas, wherein the device includes a vent in the canister that is sealed during storage and is opened prior to use to reduce the pressure inside the canister and permit full expansion of the expandable inner container.

* * * * *